United States Patent
Schlosberg et al.

(10) Patent No.: US 7,241,930 B2
(45) Date of Patent: Jul. 10, 2007

(54) TRANSALKYLATION OF AROMATIC FLUIDS

(75) Inventors: Richard Henry Schlosberg, Bridgewater, TX (US); Edmund John Mozeleski, Califon, NJ (US); Francisco M. Benitez, Houston, TX (US); Steven M. Silverberg, Seabrook, TX (US); Terry Eugene Helton, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 427 days.

(21) Appl. No.: 10/414,658

(22) Filed: Apr. 16, 2003

(65) Prior Publication Data

US 2004/0143146 A9 Jul. 22, 2004

(51) Int. Cl.
*C07C 5/22* (2006.01)
(52) U.S. Cl. .................................... 585/475; 585/471
(58) Field of Classification Search ................ 585/475, 585/471
See application file for complete search history.

(56) References Cited

U.S. PATENT DOCUMENTS

| | | | |
|---|---|---|---|
| 2,837,583 A | 6/1958 | Lien et al. ............... 260/671 |
| 3,308,069 A | 3/1967 | Wadlinger et al. .......... 252/455 |
| 3,702,886 A | 11/1972 | Argauer et al. ............. 423/328 |
| 3,709,979 A | 1/1973 | Chu ........................... 423/328 |
| 3,832,449 A | 8/1974 | Rosinski et al. ............ 423/328 |
| 4,016,245 A | 4/1977 | Plank et al. ................ 423/328 |
| 4,076,842 A | 2/1978 | Plank et al. ................ 423/328 |
| 4,784,745 A | 11/1988 | Nace ........................... 208/74 |
| 4,956,514 A | 9/1990 | Chu ........................... 585/533 |
| 5,082,983 A | 1/1992 | Breckenridge et al. ..... 585/475 |
| 5,198,203 A | 3/1993 | Kresge et al. .............. 423/718 |
| 5,236,575 A | 8/1993 | Bennett et al. ............... 208/46 |
| 5,302,769 A | 4/1994 | Marler et al. ............... 585/455 |
| 5,336,478 A | 8/1994 | Dwyer et al. ............... 423/708 |
| 6,297,417 B1 | 10/2001 | Samson et al. ............. 585/448 |

FOREIGN PATENT DOCUMENTS

| | | |
|---|---|---|
| EP | 0494315 A1 | 2/1992 |
| GB | 1108177 | 4/1968 |
| JP | 31 61556 B2 | 8/1993 |

*Primary Examiner*—Thuan Dinh Dang
(74) *Attorney, Agent, or Firm*—Andrew B. Griffis

(57) ABSTRACT

A process for making an ethylated polycyclic aromatic compound in a mixed aromatic fluid, the process comprising contacting the mixed aromatic fluid containing a polycyclic aromatic compound and a monocyclic aromatic compound having an ethyl substituent in the presence of an acid catalyst under conditions sufficient to effect transalkylation to form the ethylated polycyclic compound and a de-ethylated monocyclic aromatic compound and removal of the de-ethylated monocyclic aromatic compound. A process for decreasing naphthalene concentration in a naphthalene-containing aromatic fluid by acid catalyzed transalkylation of an alkylbenzene and naphthalene to form benzene and an alkylnaphthalene.

9 Claims, 1 Drawing Sheet

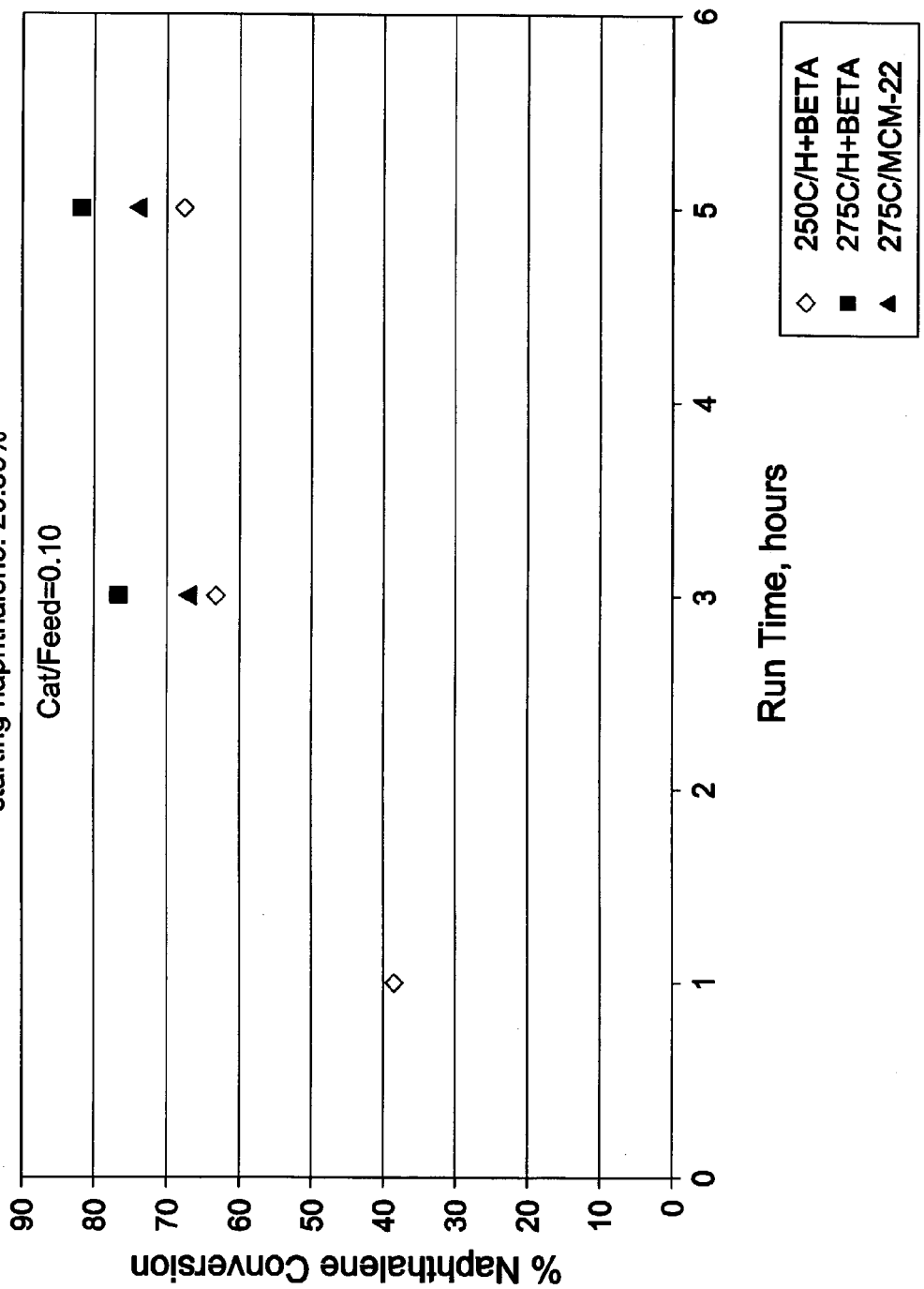

TRANSALKYLATION OF AROMATIC FLUIDS

FIELD OF THE INVENTION

The present invention relates to transalkylation of alkylated mononuclear aromatic compounds in the presence of polycyclic aromatic compounds. More particularly, the present invention relates to the selective transalkylation of a mixture of mononuclear aromatic compounds in the presence of a bicyclic aromatic compound.

Large-scale refinery production separates crude oil into many fractions one of which is known as virgin naphtha. Virgin naphtha is often reformed to make aromatic naphtha or reformate for motor gasoline blending and chemicals recovery. The fractionation process is often a complex distillation that primarily relies on the difference in the boiling points of the components of the reformate for separation into various fractions. Many of these fractions may contain naphthalene. Consequently, there exists a need for aromatic fluids having a reduced naphthalene concentration and a process for producing aromatic fluids having a reduced concentration of naphthalene. These processes permit naphthalene-containing aromatic fluid and ethylbenzene-containing fluid to be converted into products with enhanced value and to recover by-products for recycling.

Additionally, some of the refinery fractions contain a mixture of xylene and ethylbenzene. The xylene comprises at least one of 1,2-dimethylbenzene, 1,3-dimethylbenzene and 1,4-dimethylbenzene. Removal of the ethylbenzene from the xylene is desirable, but complicated by the similar boiling points of the xylene and ethylbenzene. The problems of removing naphthalene from aromatic fluids and ethylbenzene from a mixture of xylene and ethylbenzene can be solved by transalkylation of the naphthalene containing aromatic fluid with a mixture of xylene and ethylbenzene under conditions for the selective de-ethylation of ethylbenzene and the ethylation of naphthalene. This results in increased value for a naphthalene-depleted aromatic fluid and for ethylbenzene-deplete xylene. Also this permits the recovery of benzene for recycle into higher value products.

SUMMARY OF THE INVENTION

The present invention provides an aromatic fluid having a reduced concentration of naphthalene and a process for producing an aromatic fluid having a reduced naphthalene concentration. The aromatic fluid comprises at least one aromatic compound, typically a mixture of two or more aromatic compounds. The aromatic fluid may comprise an aromatic compound which is fluid at ambient temperature; may comprise an aromatic compound that would be solid at ambient temperature, but is fluid under transalkylation conditions; or may comprise a mixture of an aromatic compound, that would be a solid at ambient temperature, dissolve in a liquid aromatic compound. One embodiment of the present invention also provides a process for recovering benzene from a C-8 aromatic fluid. The C-8 aromatic fluid comprises at least one eight-carbon compound having an aromatic ring, preferably a carbocyclic aromatic ring. The C-8 aromatic fluid typically comprises at least one of ethylbenzene, 1,2-dimethylbenzene, 1,3-dimethylbenzene and 1,4-dimethylbenzene. In one embodiment according to the present invention, the C-8 aromatic fluid comprises ethylbenzene, 1,2-dimethylbenzene, 1,3-dimethylbenzene and 1,4-dimethylbenzene. In another embodiment according to the present invention, the C-8 aromatic fluid consists essentially of ethylbenzene, 1,2-dimethylbenzene, 1,3-dimethylbenzene and 1,4-dimethylbenzene.

One embodiment of the present invention provides a process of reducing the naphthalene concentration in a mixture of aromatic fluids by conversion of the naphthalene to an alkylnaphthalene. In one embodiment according to the present invention, the naphthalene concentration is reduced to less than about 1000 ppm. Another embodiment according to the present invention provides a process of removing ethylbenzene from mixed aromatic fluids by transalkylation of an aromatic compound with ethylbenzene.

One embodiment according to the present invention is a method of reducing unsubstituted polycyclic aromatic compound concentration in a mixed aromatic fluid by contacting the mixed aromatic fluid containing a polycyclic aromatic compound with an ethyl substituted monocyclic aromatic compound in the presence of an acid catalyst under conditions sufficient to effect transalkylation to form an ethylated polycyclic compound and a de-ethylated monocyclic aromatic compound and removing the de-ethylated monocyclic aromatic compound from the mixture.

One embodiment according to the present invention is a process of reducing naphthalene concentration in a mixture of aromatic fluids by contacting the mixture of aromatic fluids containing naphthalene and an ethyl substituted monocyclic aromatic compound in the presence of an acid catalyst under conditions sufficient to effect transalkylation to form ethylnaphthalene and a de-ethylated monocyclic aromatic compound and removing the de-ethylated monocyclic aromatic compound.

In another embodiment according to the present invention, a process for decreasing naphthalene concentration in a naphthalene-containing aromatic fluid comprises mixing the naphthalene-containing aromatic fluid with an ethylbenzene-containing fluid to form a mixed aromatic fluid; contacting the mixed aromatic fluid with an acid catalyst under conditions sufficient to form a naphthalene-depleted aromatic fluid comprising ethylnaphthalene and benzene; and separating the benzene from the naphthalene-depleted fluid.

In another embodiment according to the present invention, a process for selectively transalkylating naphthalene in a mixture of aromatic compounds comprises contacting the mixture of aromatic compounds, comprising naphthalene and an monocyclic alkylated aromatic compound, with an acid catalyst under conditions sufficient to effect transalkylation of the naphthalene to form ethylnaphthalene and benzene, wherein the mononuclear alkylated aromatic compound comprises ethylbenzene and methylated benzene compounds and wherein the ratio of ethylbenzene to methylated benzene compounds decreases during transalkylation.

In another embodiment according to the present invention, a process for reduction of naphthalene concentration in a mixed aromatic fluid comprises mixing a C-8 aromatic fluid comprising ethylbenzene with a naphthalene-containing aromatic fluid to form a mixed aromatic fluid; contacting the mixed aromatic fluid with an acid catalyst under conditions sufficient to effect transalkylation to form benzene and a naphthalene-depleted mixed aromatic fluid; and separating the benzene from the naphthalene-depleted aromatic fluid.

In another embodiment according to the present invention, a process for reducing naphthalene concentration in a mixed aromatic fluid, the process comprises contacting an acid catalyst and the mixed aromatic fluid under conditions sufficient to form ethylnaphthalene, wherein the mixed aromatic fluid comprises 1,2,4-trimethylbenzene; 1,2,3-trimethylbenzene; m-cymene; a mixture of alkylbenzene compounds having from 1 to 4 alkyl substituents, each alkyl substituent having from 1 to 4 carbon atoms and the alkylbenzene compounds have a total number of carbon atoms ranging from 10 to 12; naphthalene; and methylnaphthalene.

In one embodiment according to the present invention, the acid catalyst is any acid of sufficient acidity to effect transalkylation. The acid catalyst comprises at least one of H+BETA, MCM-22, MCM-49 and USY, which may be used in any of the embodiments described above.

BRIEF DESCRIPTION OF THE DRAWINGS

FIG. 1 shows the % naphthalene conversion versus the run time.

DETAILED DESCRIPTION OF THE INVENTION

One embodiment according to the present invention provides aromatic fluids having a reduced naphthalene concentration and processes for producing aromatic fluids having a reduced concentration of aromatic fluids by transalkylation. Another embodiment according to the present invention provides a process of recovering benzene from C-8 aromatic fluid by transalkylation. The C-8 aromatic fluid typically comprises xylene and ethylbenzene.

One embodiment according to the present invention provides a process of reducing naphthalene concentration in a mixture of aromatic fluids by conversion of the naphthalene to an alkylnaphthalene. The present invention also provides a process of removing ethylbenzene from mixed aromatic fluids. These processes permit naphthalene-containing aromatic fluid and ethylbenzene-containing fluid to be converted into products with enhanced value and to recover by-products for recycling.

One embodiment according to the present invention provides a process for making an ethylated polycyclic aromatic compound in a mixed aromatic fluid, the process comprising contacting the mixed aromatic fluid containing a polycyclic aromatic compound and a monocyclic aromatic compound having an ethyl substituent in the presence of an acid catalyst under conditions sufficient to effect transalkylation to form the ethylated polycyclic compound and a de-ethylated monocyclic aromatic compound and removal of the de-ethylated monocyclic aromatic compound. In one embodiment according to the present invention, the polycyclic compound comprises naphthalene and the monocyclic compound comprises ethylbenzene. In one embodiment, preferably from about 20 wt % to about 90-wt % of the polycyclic compound is converted to the ethylated polycyclic compound. In one embodiment, the preferred catalyst comprises at least one zeolite selected from H+Beta, MCM-22, MCM-49 and USY.

In another embodiment according to the present invention, a process for reduction of naphthalene concentration in a mixed aromatic fluid comprises mixing a C-8 aromatic fluid comprising ethylbenzene with a naphthalene-containing aromatic fluid to form a mixed aromatic fluid; contacting the mixed aromatic fluid with an acid catalyst under conditions sufficient to effect transalkylation to form benzene and a naphthalene-depleted mixed aromatic fluid; and separating the benzene from the naphthalene-depleted aromatic fluid. The naphthalene-containing aromatic fluid is exemplified by Aromatic 150™ and Aromatic 200™ Fluids sold by ExxonMobil Chemical Company. In one embodiment, preferably from about 20 wt % to about 90-wt % of the polycyclic compound is converted to the ethylated polycyclic compound. In one embodiment, the preferred catalyst comprises at least one zeolite selected from H+Beta, MCM-22, MCM-49 and USY. Preferably the naphthalene-depleted fluid comprises less than about 1000 ppm naphthalene. The naphthalene concentration in the naphthalene-depleted mixed aromatic fluid may be further reduced by mixing the naphthalene-depleted mixed aromatic fluid with a C-8 aromatic fluid comprising ethylbenzene to form a reduced naphthalene containing mixed aromatic fluid; contacting the reduced naphthalene containing mixed aromatic fluid with an acid catalyst under conditions sufficient to effect further transalkylation to form benzene and a naphthalene-depleted mixed aromatic fluid having less than about 1000 ppm naphthalene; and separating the benzene from the naphthalene-depleted aromatic fluid having less than about 1000 ppm naphthalene.

A process for reducing naphthalene concentration in a mixed aromatic fluid, the process comprising contacting an acid catalyst and the mixed aromatic fluid under conditions sufficient to form ethylnaphthalene, wherein the mixed aromatic fluid comprises 1,2,4-trimethylbenzene; 1,2,3-trimethylbenzene; m-cymene; a mixture of alkylbenzene compounds having from 1 to 4 alkyl substituents, each alkyl substituent having from 1 to 4 carbon atoms and the total carbon atoms in the alkylbenzene compounds is 10, 11 or 12; naphthalene; and methylnaphthalene. In one embodiment, preferably from about 20 wt % to about 90-wt % of the naphthalene is converted to the ethylnaphthalene. In one embodiment, the preferred catalyst comprises at least one zeolite selected from H+Beta, MCM-22, MCM-49 and USY. In one embodiment, the naphthalene concentration in the product is less than about 1000 ppm. In one embodiment according to the present invention, the mixed aromatic fluid comprises Aromatic 150™ or Aromatic 200™ Fluid sold by ExxonMobil Chemical Company.

A process for selectively transalkylating naphthalene in a mixture of aromatic compounds, the process comprising contacting the mixture of aromatic compounds comprising naphthalene and mononuclear alkylated aromatic compounds with an acid catalyst under conditions sufficient to effect transalkylation of the naphthalene to form ethylnaphthalene and benzene, wherein the mononuclear alkylated aromatic compounds comprise ethylbenzene and methylated benzene compounds and wherein the ratio of ethylbenzene to methylated benzene compounds decreases during the transalkylation process. In one embodiment according to the present invention, the ratio of naphthalene concentration in the mixture of aromatic compounds to the naphthalene concentration after transalkylation of the mixture of compounds ranges from about 80 to about 200. In one embodiment, preferably from about 20 wt % to about 90-wt % of the naphthalene is converted to the ethylnaphthalene. In one embodiment, the preferred catalyst comprises at least one zeolite selected from H+Beta, MCM-22, MCM-49 and USY. In one embodiment, the naphthalene concentration in the product after transalkylation is less than about 1000 ppm. The process may further comprise adding mononuclear alkylated aromatic compounds to the product mixture resulting from the initial transalkylation reaction and effecting further transalkylation to further reduce the naphthalene concentration.

A process for decreasing naphthalene concentration in a naphthalene-containing aromatic fluid, the process comprising mixing the naphthalene-containing aromatic fluid with an ethylbenzene-containing fluid to form a mixed aromatic fluid; contacting the mixed aromatic fluid with an acid catalyst under conditions sufficient to form a naphthalene-depleted aromatic fluid comprising ethylnaphthalene and benzene; and separation of the benzene from the naphthalene-depleted fluid. In one embodiment, preferably from about 20 wt % to about 90-wt % of the naphthalene is converted to the ethylnaphthalene. In one embodiment, the preferred catalyst comprises at least one zeolite selected from H+Beta, MCM-22, MCM-49 and USY. In one embodiment, the naphthalene concentration in the naphthalene-depleted aromatic fluid after transalkylation is less than about 1000 ppm. In another embodiment, the naphthalene concentration in the naphthalene-depleted fluid may be further reduced by the optional step of adding additional ethylbenzene-containing fluid to the naphthalene-depleted fluid and effecting further transalkylation in the presence of an acid catalyst under conditions to form additional ethylnaphthalene and benzene. The separation of benzene from any embodiment described herein may be accomplished by conventional methods including, but not limited to, distillation and extraction.

Feedstock

The aromatic fluid containing naphthalene useful in this process can be derived from a substantially dealkylated feedstock. The type of aromatic fluid feedstock useful in one embodiment of the present invention comprises one or more fused-ring polycyclic aromatic compounds, although assemblies of two or more cyclic systems, either single ring cyclics or aromatics or fused systems may also be present. In one embodiment according to the present invention the mixed aromatic fluid comprises 1,2,4-trimethylbenzene; 1,2,3-trimethylbenzene; m-cymene; a mixture of alkylbenzene compounds having from 1 to 4 alkyl substituents, each alkyl substituent having from 1 to 4 carbon atoms and the alkylbenzene compounds have a total number of carbon atoms ranging from 10 to 12; naphthalene; and methylnaphthalene.

The polycyclic aromatic compound is typically obtained from catalytic reforming operations but may also be obtained from cracking operations, e.g. fluidized bed catalytic cracking (FCC) or moving bed Thermofor catalytic cracking (TCC). Typically, these feed stocks have a hydrogen content of no greater than about 12.5 wt. % and API gravity no greater than 25 and an aromatic content no less than 50 wt. %.

A substantially dealkylated feedstock is a product that was formerly an alkyl aromatic compound, or mixture of alkyl aromatic compounds, that contained bulky relatively large alkyl group side chains affixed to the aromatic moiety. The dealkylated product is the aromatic compound having no bulky side chain alkyl group. Representative examples of the aromatic compound include phenanthrene, anthracene, dibenzothiophene, fluoroanthene, fluorene, benzothiophene, acenaphthene, biphenyl or naphthalene.

During acid catalyzed cracking and similar reactions, prior dealkylation generally will remove side chains of greater than 5 carbon atoms while leaving behind primarily methyl or ethyl groups on the aromatic compounds. Thus, for purposes of this invention, the polycyclic aromatic compounds can include substantially dealkylated aromatic compounds which contain small alkyl groups, such as methyl and sometimes ethyl and the like, remaining as side chains, but with relatively few large alkyl groups, e.g. the $C_3$ to $C_9$ groups remaining.

In one embodiment, the polycyclic aromatic feedstock comprises a mixture of polycyclic compounds, dealkylated or substantially dealkylated, which would be found in a refinery by-product stream. Alternatively, the polyaromatic feedstock comprises a relatively pure feed consisting essentially of one type of polycyclic aromatic compound.

Representative examples of suitable polycyclic aromatic refinery by-product derived feedstocks include reformate, light cycle oils and heavy cycle oils from catalytic cracking or pyrolysis processes. Other examples of suitable feedstocks include the liquid product from a delayed or fluid bed coking process, such as a coker gas oil, an aromatics-rich fraction produced by lubricant refining, e.g., furfural extraction. Other sources of suitable feedstocks include a heavy crude fraction obtained by crude fractional distillation.

Specifically, the polycyclic aromatic compound contemplated contains at least 2 cyclic groups and up to at least 5 cyclic groups. It can be a hydrocarbon containing up to 5 or more benzene rings in any arrangement including fixed benzene rings in linear arrangement. It can be almost entirely or predominantly carbocyclic and can include or be part of a heterocyclic system in which at least one of the cyclic elements of the molecule contains at least one heteroatom such as sulfur, nitrogen and/or oxygen.

In one embodiment according to the present invention the mixture of aromatic compounds may be Aromatic 150™ or Aromatic 200™ fluids sold by. ExxonMobil Chemical Company. Aromatic 150™ fluid comprises approximately fifty components with some of the principle components comprising about 1.7 wt. % of 1,2,4-trimethylbenzene; about 3.0 wt. % of 1,2,3-trimethylbenzene and meta-cumene; a mixture of about 81.6 wt. % C-10 to C-12 benzene compounds, having one or more substituents selected from methyl, ethyl, propyl, and butyl; about 8.6 wt. % naphthalene; and about 0.3 wt. % methylnaphthalene.

Alternatively, the Aromatic 150™ fluid may be distilled at atmospheric pressure to remove about 60 wt. % of the lighter components to leave an Aromatic 150™ fluid concentrate that is about 40 wt. % of the total material prior to distillation. The Aromatic 150™ fluid concentrate comprises about 20.4 wt. % naphthalene.

Aromatic 200™ fluid comprises approximately 25 to 30 components with some of the principle components comprising naphthalene (10 wt %); various alkylnaphthalenes (75 wt %), including 2-methylnaphthalene (26 wt %), 1-methylnaphthalene (13 wt %), 2-ethylnaphthalene (2%), dimethyl naphthalenes (18 wt %), and trimethyl naphthalenes (7 wt %); and the remaining 15 wt % comprises primarily alkylbenzenes, as determined by gas chromatographic analysis.

Aromatic 100™ fluid may also be used. Aromatic 100™ fluid comprises a mixture of components with some of the principle components comprising alkylbenzenes having 9 to 10 carbon atoms, the alkyl groups primarily being methyl and ethyl groups, and some of the principle components comprising propylbenzene (5%), ethylmethylbenzenes (28%), 1,3,5-trimethylbenzene (10%), and 1,2,4-trimethylbenzene (32%).

Alkylating Agent

The polycyclic aromatic compound is contacted with an aromatic transalkylating agent, typically, an alkyl-substituted monocyclic aromatic compound. The alkyl-substituted monocyclic aromatic compound has from one to four short chain alkyl substituents. Preferably, the short chain alkyl substituent contains from 1 to 2 carbon atoms, i.e., methyl and ethyl substituents. Most preferably the short chain hydrocarbon is ethyl, in which instance the monocyclic aromatic compound is a transethylating agent. Representative examples of transalkylating agents include ethylbenzene, toluene and, ortho-, meta- or para-methylethylbenzene (e.g. o-, m- or p-xylene).

The source of monocyclic aromatic compound comprises a reformate fraction or any other ethyl substituted monocyclic aromatic-rich feed. Specific examples include a reformate from a swing bed or moving bed reformer. Although a most useful source of these monocyclic aromatic compounds is a reformate fraction, other useful sources include pyrolysis gasoline, coker naphtha, methanol-to-gasoline, or other zeolite catalyst olefin or oxygenate conversion process wherein significant aromatics product is obtained. Another source is the heavy side product of various aromatics conversion processes (e.g., toluene disproportionation and xylene isomerization).

Another advantage to using the monocyclic aromatic compound as a transalkylating agent, instead of alkylating with an alcohol or alkylhalide, is the resulting conversion of the monocyclic aromatic compound to a gasoline boiling range product when the monocyclic aromatic compound is an ethylalkylbenzene or to benzene when the monocyclic aromatic compound is ethylbenzene. The polyalkylated alkylating agents, having both an ethyl substituent and at least one methyl substituent, are not entirely dealkylated by the reaction. The ethyl substituent is selectively transferred preferentially over a methyl substituent when the ethyl substituent and the methyl substituent are on the same mononuclear aromatic compound. The ethyl substituent is also selectively transferred from ethylbenzene in a mixture also containing methyl- or polymethylbenzene compounds.

An advantage of using the monocyclic aromatic compound as a transalkylating agent, instead of alkylating with an alcohol or alkylhalide, is the resulting conversion of the polyalkylated monocyclic aromatic compound to a gasoline boiling range product or the conversion of ethylbenzene to benzene, which may be separated and recycled.

In one embodiment according to the present invention, the alkylating agent is a C-8 aromatic fluid comprising xylene and ethylbenzene. In another embodiment according to the present invention, the alkylating agent is a C-8 aromatic fluid consisting primarily of xylene and ethylbenzene.

The transalkylation of a polycyclic aromatic compound, such as naphthalene, with an alkylsubstituted monocyclic aromatic compound, such as ethylbenzene, is an equilibrium reaction. As shown in FIG. 1, the equilibrium is established faster at higher temperatures. The optimal temperature for a particular catalyst, naphthalene-containing feed and alkylating agent may be determined by routine testing.

The equilibrium of the transalkylation is affected by the ratio of the alkylsubstituted monocyclic aromatic compound to naphthalene-containing aromatic compound containing fluid. A higher mono-alkylsubstituted benzene to naphthalene ratio increases the equilibrium concentration of the substituted naphthalene and benzene in the transalkylation. By controlling the ratio of mono-alkylsubstituted benzene to naphthalene-containing aromatic compound containing fluid, while holding other parameters constant, the concentration of naphthalene in the transalkylation product mixture may be minimized and the concentration of benzene maximized. In one embodiment according to the present invention, the naphthalene-containing aromatic fluid is contacted with an acidic catalyst in the presence of an alkylsubstituted benzene containing fluid, wherein the ratio of the alkylsubstituted benzene to naphthalene ranges from about 10 to about 1 and more preferably from about 5 to about 1.

Alternatively, a larger naphthalene to alkylsubstituted benzene ratio increases the equilibrium concentration of benzene formed during the transalkylation. In one embodiment according to the present invention, the naphthalene-containing aromatic fluid is contacted with an acidic catalyst in the presence of an alkylsubstituted benzene containing fluid, wherein the ratio of the naphthalene to alkylsubstituted benzene ranges from about 1:1 to preferably about 1:10. One embodiment according to the present invention is a process of recovering benzene from a C-8 aromatic fluid comprising mixing a C-8 aromatic compound fluid with a naphthalene-containing aromatic compound containing fluid in the presence of an acidic catalyst under conditions sufficient to effect transalkylation to form a benzene containing, naphthalene depleted aromatic fluid and separating the benzene from the benzene containing, naphthalene depleted aromatic fluid. A naphthalene depleted aromatic fluid refers to a reduction of more than about 10% of the naphthalene present in the starting naphthalene-containing aromatic fluid. In one embodiment of the process of recovering benzene from a C-8 aromatic compound containing fluid, the C-8 aromatic fluid comprises primarily xylene and ethylbenzene. In another embodiment of the process of recovering benzene from a C-8 aromatic compound containing fluid, the ratio of the naphthalene to alkylsubstituted benzene ranges from about 1 to about 10, preferably from about 1 to about 5.

Also, the equilibrium is affected by the catalyst, as shown in FIG. 1. Catalysts.

The catalyst used in the process of this invention is an acid catalyst. The classes of suitable catalysts include crystalline metallosilicates, such as zeolites, including molecular sieves. Other acidic oxides may also be suitable. These solid catalysts are useful in fluid and fixed bed catalysis, and, being heterogeneous to the reactants, are readily separable therefrom.

The choice of catalyst most useful for this process is dependent upon the feedstock and, in some cases, to the product desired. For example, with the larger polycyclic aromatic that contains over about 2 aromatic rings, the pore size of the catalyst must be sufficiently large since the pore size constraints of the zeolite can hinder admittance of these bulky molecules. Thus, the preferred catalysts for this invention are the large pore zeolitic behaving catalytic materials, including H+Beta, MCM-22, MCM-49, and USY. These zeolitic catalytic materials are exemplified by those that, in their aluminosilicate form would have a Constraint Index ranging from up to about 2, preferably from about 0.2 to 2 and more preferably, less than 1.

Reference is here made to U.S. Pat. No. 4,784,745 for a definition of Constraint Index and a description of how this value is measured. The preferred catalytic materials having the appropriate functionality include mordenite, zeolite beta, faujasites such as zeolite Y, and Ultra Stable Y (USY).

Other zeolitic catalytic materials are useful in this process particularly with feeds that are predominantly composed of polycyclic systems having two rings, such as naphthalene and alkyl-substituted naphthalenes such as monoethylnaphthalene. A particular class of catalytic materials having the appropriate functionality, in any embodiment disclosed herein, includes, but is not limited to, those having the topology of ZSM-5, ZSM-11, ZSM-12, ZSM-22, ZSM-23, ZSM-35, ZSM-48, ZSM-50 and MCM-22. These zeolites are described in the following patent and patent applications which are fully incorporated by reference: ZSM-5 in U.S. Pat. No. 3,702,886; ZSM-11 in U.S. Pat. No. 3,709,979; ZSM-12 in U.S. Pat. No. 3,832,449; ZSM-22 in U.S. patent applications Ser. Nos. 373,451 and 373,452 both filed on Apr. 30, 1982; ZSM-23 in U.S. Pat. No. 4,076,842; ZSM-35 in U.S. Pat. No. 4,016,245; ZSM-48 in U.S. application Ser. No. 13,640, filed on Feb. 21, 1979; ZSM-50 in U.S. Ser. No. 705,822, filed Feb. 26, 1985 MCM-22 in U.S. Pat. No.

4,956,514; zeolite beta in U.S. Pat. No. 3,308,069; and MCM-49 in U.S. Pat. No. 5,236,575.

The catalytic materials described are exemplary of the topology and pore structure of suitable acid-acting refractory solids; useful catalysts are not confined to the aluminosilicates, and other refractory solid materials which have the desired acid activity, pore structure and topology may also be used. The crystalline zeolites have a porous framework. The framework typically comprises primarily silicon tetrahedrally coordinated and interconnected with oxygen bridges. Other framework components, for example, may include Group IIIB elements of the Periodic Table, e.g. aluminum, boron and gallium. Other elements such as phosphorus and iron may be included as framework components. Aluminum phosphates and silico-aluminum phosphates are specifically contemplated. The zeolite designations referred to above, for example, define the topology only and do not restrict the compositions of the zeolitic-behaving catalytic components.

The catalyst should have sufficient acid activity and selectivity to promote the alkylation/transalkylation, more specifically ethylation/transethylation, reactions at reasonable temperatures and catalyst space velocities. Transalkylation is specifically defined herein as the transfer of one or more lower alkyl groups, such as ethyl, from the alkyl substituted monocyclic aromatic compound to the polycyclic aromatic compound, such as naphthalene.

The active component of the catalyst, e.g., the zeolite, will usually be used in combination with a binder or substrate because the particle sizes of the pure zeolitic behaving materials are often too small and lead to an excessive pressure drop in a catalyst bed. This binder or substrate, which is preferably used in this service, is suitably any refractory binder material. Examples of these materials are well known and typically include silica, silica-alumina, silica-zirconia, silica-titania, alumina, Titania or zirconia. The catalyst may be in the form of a powder or extrudate. The catalyst comprises the zeolite as an active component in the range of 0 to 100 wt % and a binder in the range of from 0 wt % to about 40 wt %.

The particle size and the nature of the conversion catalyst will usually be determined by the type of conversion process which is being carried out, such as: a down-flow, liquid phase, fixed bed process; an up-flow, fixed bed, liquid phase process; an ebullating, fixed fluidized bed liquid or gas phase process; or a liquid or gas phase, transport, fluidized bed process, as noted above, with the fixed-bed type of operation preferred.

The lower limits on catalyst activity and on reactive conditions are sufficient to convert at least about 20 wt. % and preferably at least about 50 wt. % of the polycyclic aromatic compounds in the feed. Conversion of the polycyclic aromatic compounds refers to the addition of molecular weight (e.g. ethyl) side chains. The total number of moles of polycyclic aromatic compounds in the product will normally be about the same as the total moles of polycyclic aromatic compounds in the feed to the reactor. The degree of ethylation of the naphthalene, i.e., the degree of naphthalene reduction, ranges from about 20 to 50 wt %, preferably from at least about 40%. The degree of ethylation of the polycyclic aromatic compound, preferably naphthalene, ranges from at least about 10 wt. %, more preferably from at least about 20 wt %, even more preferably from at least about 30 wt %, and most preferably from at least about 50 wt %. The degree of ethylation of naphthalene is most preferred when the concentration of naphthalene in the total mixture of aromatic compounds is less than about 1000 ppm.

With most catalysts, the following reaction conditions can be used in any of the embodiments disclosed herein. Temperatures may range from about 270° C. to 600° C. (518° F. to 1100° F.), more preferably at about 275° C. Although fluidized, fixed or moving bed reactors can be used, the relative ratios of feed to catalyst, as applied to fixed beds will be provided. Weight hourly space velocities (WHSV) of from about 0.5 to 15, more specifically from about 1 to about 10 will usually give good results. Pressures may range from atmospheric, or even subatmospheric to relatively high pressures and usually will range from about 1 to about 1000 psig. Oil partial pressures will normally range from about 100 psia to about 500 psia. Hydrogen is not essential, but the process may benefit from its presence, particularly in extending catalyst life. When hydrogen is added it typically ranges from about 0.5:1.0, to 5.0:1.0, expressed in terms of hydrogen to hydrocarbon mole ratio. The mole ratio of polycyclic aromatic to monocyclic aromatic falls within the range of about 1:10 to 10:1, more specifically from about 1:5 to 5:1.

The catalyst life may be prolonged by removing contaminants such as water and oxygenates. Any solid drying agent known to those skilled in the art may be used to reduce the water concentration in the alkylation or transalkylation feedstream, such as those disclosed in U.S. Pat. No. 6,297,417, which is fully incorporated by reference. Non-limiting examples of suitable drying agents include aluminas, silicas, silica-aluminas, and zeolites. The aluminas, silicas, and silica-aluminas may be crystalline or amorphous. Zeolites are crystalline microporous aluminosilicates that have framework structures formally constructed from ($SiO_4$) and ($AlO_4$) tetrahedra that share vertices. Each framework topology contains a regular array of pores, channels, and/or cages that vary in size, shape, and dimensionality. Examples of suitable zeolites include erionite, chabazite, rho, gismondine, Linde 13X, Linde type A (LTA) molecular sieves, such as 3A, 4A, and 5A. A description of these zeolites, their structures, properties, and methods of synthesis can be found in the following references: Zeolite Molecular Sieves, Donald W. Breck, John Wiley & Sons, 1974; Atlas of Zeolite Structure Types, 3rd ed., W. M. Meier and D. H. Olson, Butterworth-Heinemann, 1992; and Handbook of Molecular Sieves, R. Szostak, Chapman & Hall, N.Y., 1992; which are incorporated herein by reference. Many of the suitable aluminas, silicas, silica-aluminas, and zeolites are commercially available. The preferred drying agents comprise LTA zeolites, including 3A, 4A, and 5A, in addition to Linde zeolite 13X and Selexsorb CDO™ brand alumina.

Benzene and substituted benzenes can also contain oxygen and organic oxygenates. The equilibrium concentration of molecular oxygen which is dissolved in unsubstituted benzene at about 23° C. is about 300 ppm by weight, as measured by an oxygen analyzer, such as an Orbisphere Oxygen Analyzer Model 26083 or any other conventional method of oxygen analysis. "Organic oxygenates" are defined as organic compounds which comprise carbon, hydrogen, and oxygen. Non-limiting examples of organic oxygenates, which may be found in benzene and substituted benzenes, include organic hydroperoxides, ketones, aldehydes, and phenols. The organic oxygenates may be natural impurities in the aromatic hydrocarbon as it is obtained from coal tar, or from a gasoline refinery, or from a benzene extraction unit, or a hydrodealkylation unit typically present at naphtha steam cracker facilities. Alternatively, the organic oxygenates may be produced by the reaction of oxygen with hydrocarbons present in the feed. In addition to oxygen and oxygenates, aromatic hydrocarbons may also contain small amounts of other impurities, including nitrogen-containing organic compounds, typically for example, traces of extraction solvents, such as N-methylpyrrolidone.

The lifetime of any alkylation/transalkylation catalyst can be increased by the above-described process to remove water and/or organic oxygenates.

EXAMPLE 1

All of the transalkylation reactions were conducted in Swagelock® stainless steel mini-reactors, having internal volumes of 13 cc, that were heated to about 275° C. by placing the mini-reactor into a silicone oil bath preheated to 275° C. The catalyst to Aromatic 150 fluid ratio was about 0.1 gram/gram. The reaction time is about five hours from the time the mini-reactor was placed into the preheated silicone oil bath to removal of the mini-reactor from the preheated silicone oil bath. The reaction mixture was not stirred. The reactor. contents were cooled to room temperature by submersing the reactor into water. After the reactor contents were cooled to room temperature, the liquid phase was separated from the solid catalyst by decanting the liquid from the solids. No solvent was added. The liquid phase was analyzed by gas chromatography using a Hewlett-Packard 6890 with a 30-meter non-polar HP-1 (cross-linked methylsiloxane) column. The starting temperature of the gas chromatograph column oven was 10° C. and it was programmed to heat to 300° C. at a rate of 5° C. per minute. A response factor of 1 was used for all components.

TABLE 1

Naphthalene Reduction In Aromatic 150 Fluid Under Conditions in Example 1

| Catalyst Description | % Naphthalene Removed |
|---|---|
| Valfor C-806β H + zeolite beta, powder | 89.8 |
| 65% MCM-22, 35% Al$_2$O$_3$ binder | 68.1 |
| 65% MCM-22, 35% Al$_2$O$_3$ binder | 70.8 |
| 80% MCM-22, 20% Al$_2$O$_3$ binder | 58.5 |
| 100% MCM-22, 0% Al$_2$O$_3$ binder | 73.9 |
| 100% MCM-22, 0% Al$_2$O$_3$ binder | 70.3 |
| 40% MCM-22, 40% Mordenite, 20% Al$_2$O$_3$ binder | 56.4 |
| 65% Tosoh 360 HUA USY, 35% Al$_2$O$_3$ binder | 68.6 |
| 65% Beta, 35% Al$_2$O$_3$ binder | 39.6 |

EXAMPLE 2

The general procedure of Example 1 was used except that the Aromatic Fluid 150 concentrate containing about 20.4% naphthalene was heated in the presence of H+BETA catalyst for 5 hours at about 275° C. Approximately 82% of the naphthalene was converted to ethylnaphthalene.

EXAMPLE 3

The general procedure of Example 1 was used except that the Aromatic Fluid 150 concentrate containing about 20.4% naphthalene was heated in the presence of MCM-22 catalyst, as a powder, for 5 hours at about 275° C. Approximately 74% of the naphthalene was converted to ethylnaphthalene.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A process for decreasing naphthalene concentration in a naplithalene-containing aromatic fluid, the process comprising mixing the naphthalene-containing aromatic fluid with an ethylbenzene-containing fluid to form a mixed aromatic fluid;

contacting the mixed aromatic fluid with an acid catalyst, wherein said acid catalyst is a zeolite, under conditions sufficient to form a naphthalene-depleted aromatic fluid comprising ethylnaphthalene and benzene; and separating at least a portion of the benzene from the naphthalene-depleted fluid.

2. The process of claim 1, wherein the zeolite is at least one of H+Beta, MCM-22 MCM-49, and USY.

3. The process of claim 1, wherein from about 20 wt % to about 90 wt % of the naphthalene is converted to the ethylnaphthalene.

4. The process of claim 1, wherein the process is conducted at a temperature of from about 270° C. to about 600° C.

5. The process of claim 1, wherein a ratio of the naphthalene concentration in the naphthalene-containing aromatic fluid to the naphthalene concenuation in the naphthalene-depleted aromatic fluid ranges from about 80 to about 200.

6. The process of claim 1, wherein the naphthalene concentration of the naphthalene-depleted aromatic fluid is less than about 1000 ppm of the naphthalene-depleted aromatic fluid.

7. A process comprising:

(a) mixing a naphthalene-containing aromatic fluid with an ethylbenzene-containing fluid to form a mixed aromatic fluid;

(b) contacting said mixed aromatic fluid with a zeolite under conditions sufficient to form a naphthalene-depleted aromatic fluid comprising ethylnaphthalene and benzene; and then (c) separating at least a portion of the beuzene from the naphthalene-depleted fluid.

8. The process of claim 7, wherein said contacting with said zeolite is conducted at a temperature of from about 270° C. to about 600° C.

9. The process of claim 7, wherein said ethylbenzene-containing fluid in step (a) further comprises at least one species selected from toluene and xylenes.

* * * * *